US011103714B2

(12) United States Patent
Barror et al.

(10) Patent No.: US 11,103,714 B2
(45) Date of Patent: Aug. 31, 2021

(54) SEALED IMPLANTABLE MEDICAL DEVICE AND METHOD OF FORMING SAME

(71) Applicant: Medtronic, Inc., Minneapolis, MN (US)

(72) Inventors: Michael W. Barror, Gilbert, AZ (US); John K. Day, Chandler, AZ (US); David A. Ruben, Mesa, AZ (US); James D. Bradley, Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 286 days.

(21) Appl. No.: 16/405,032

(22) Filed: May 7, 2019

(65) Prior Publication Data

US 2019/0255335 A1    Aug. 22, 2019

Related U.S. Application Data

(63) Continuation of application No. 15/196,643, filed on Jun. 29, 2016, now abandoned.
(Continued)

(51) Int. Cl.
*A61N 1/375* (2006.01)
*A61N 1/05* (2006.01)
(Continued)

(52) U.S. Cl.
CPC .............. *A61N 1/3758* (2013.01); *A61N 1/05* (2013.01); *A61N 1/3752* (2013.01);
(Continued)

(58) Field of Classification Search
CPC .............. A61N 1/3758; A61N 1/37205; A61N 1/3752; A61N 1/3756; A61N 1/05;
(Continued)

(56) References Cited

U.S. PATENT DOCUMENTS 4,785,827 A    11/1988 Fischer
5,407,119 A    4/1995 Churchill et al.
(Continued)

FOREIGN PATENT DOCUMENTS

EP       2 875 845 A1    5/2015
WO    WO 2011/073334 A1    6/2011
(Continued)

OTHER PUBLICATIONS

Bijlard, Richard. "True Room Temperature Bonding". Healthtech event. Dec. 2014. <http://www.healthtechevent.com/wp-content/uploads/2014/12/Invenios.pdf>.
(Continued)

*Primary Examiner* — Eugene T Wu
(74) *Attorney, Agent, or Firm* — Mueting Raasch Group

(57) ABSTRACT

Various embodiments of a sealed package and a method of forming the package are disclosed. The package can include a housing extending along a housing axis between a first end and a second end, and an electronic device disposed within the housing that includes a device contact. The package can also include an external contact hermetically sealed to the housing at the first end of the housing, and a conductive member electrically connected to the external contact and the device contact such that the conductive member electrically connects the electronic device to the external contact. The conductive member is compressed between the external contact and the device contact.

20 Claims, 5 Drawing Sheets

Related U.S. Application Data

(60) Provisional application No. 62/240,339, filed on Oct. 12, 2015.

(51) Int. Cl.
*A61N 1/372* (2006.01)
*A61N 1/378* (2006.01)

(52) U.S. Cl.
CPC ......... *A61N 1/3756* (2013.01); *A61N 1/3787* (2013.01); *A61N 1/37205* (2013.01); *A61N 1/37223* (2013.01); *A61N 1/378* (2013.01); *A61N 1/3754* (2013.01)

(58) Field of Classification Search
CPC .............. A61N 1/37223; A61N 1/3787; A61N 1/3754; A61N 1/378
See application file for complete search history.

(56) References Cited

U.S. PATENT DOCUMENTS

| | | | |
|---|---|---|---|
| 5,814,091 | A | 9/1998 | Dahlberg et al. |
| 6,221,024 | B1* | 4/2001 | Miesel ................. A61B 5/0215 600/486 |
| 7,647,110 | B2 | 1/2010 | Hornfeldt et al. |
| 7,794,866 | B2 | 9/2010 | Youker et al. |
| 7,822,482 | B2 | 10/2010 | Gerber |
| 8,231,998 | B2 | 7/2012 | Sastry et al. |
| 8,267,708 | B1 | 9/2012 | Sochor |
| 8,473,056 | B2 | 6/2013 | Engmark et al. |
| 8,626,310 | B2 | 1/2014 | Barror et al. |
| 8,666,505 | B2 | 3/2014 | O'Brien et al. |
| 8,796,109 | B2 | 8/2014 | Ruben et al. |
| 2002/0138114 | A1 | 9/2002 | Gramse |
| 2002/0193859 | A1 | 12/2002 | Schulman et al. |
| 2004/0058186 | A1 | 3/2004 | Daulton |
| 2004/0103906 | A1 | 6/2004 | Schulman et al. |
| 2006/0167521 | A1 | 7/2006 | He et al. |
| 2008/0188902 | A1 | 8/2008 | Starke |
| 2009/0058361 | A1 | 3/2009 | John |
| 2009/0059468 | A1 | 3/2009 | Iyer |
| 2009/0076353 | A1* | 3/2009 | Carpenter ............ A61B 5/1459 600/310 |
| 2009/0266573 | A1 | 10/2009 | Engmark et al. |
| 2009/0308169 | A1* | 12/2009 | Mothilal ............... A61B 5/0215 73/718 |
| 2010/0267265 | A1 | 10/2010 | Dilmaghanian |
| 2011/0190842 | A1* | 8/2011 | Johnson ................ A61N 1/375 607/37 |
| 2011/0190849 | A1 | 8/2011 | Faltys et al. |
| 2012/0101540 | A1 | 4/2012 | O'Brien et al. |
| 2012/0197350 | A1* | 8/2012 | Roberts .............. A61N 1/37205 607/60 |
| 2012/0271387 | A1 | 10/2012 | Edgell et al. |
| 2013/0112650 | A1 | 5/2013 | Karam et al. |
| 2013/0196214 | A1 | 8/2013 | Scott et al. |
| 2013/0345770 | A1* | 12/2013 | Dianaty ............... A61N 1/3756 607/36 |
| 2015/0039070 | A1* | 2/2015 | Kuhn .................. A61N 1/37518 607/128 |
| 2015/0080982 | A1* | 3/2015 | Van Funderburk .......................... A61N 1/37247 607/59 |
| 2015/0321012 | A1* | 11/2015 | Cinbis ................ A61N 1/37288 607/62 |
| 2016/0185081 | A1 | 6/2016 | Sandlin et al. |
| 2016/0190052 | A1 | 6/2016 | Ruben et al. |
| 2016/0192524 | A1 | 6/2016 | Ruben |
| 2016/0296760 | A1* | 10/2016 | Sahabi ................ A61N 1/0573 |
| 2017/0127543 | A1 | 5/2017 | Day et al. |

FOREIGN PATENT DOCUMENTS

| | | |
|---|---|---|
| WO | WO 2016/106269 A1 | 6/2016 |
| WO | WO 2016/106272 A1 | 6/2016 |
| WO | WO 2016/106274 A1 | 6/2016 |
| WO | WO 2016/106323 A1 | 6/2016 |

OTHER PUBLICATIONS (PCT/US2016/048818) PCT Notification of Transmittal of the International Search Report and the Written Opinion of the International Searching Authority, dated Nov. 21, 2016, 11 pages.

Chinese Office Action with translation from CN Application No. 201680059581.3 dated Apr. 7, 2021, 16 pages.

* cited by examiner

SEALED IMPLANTABLE MEDICAL DEVICE AND METHOD OF FORMING SAME

CROSS-REFERENCE TO RELATED APPLICATIONS

This application is a continuation of U.S. patent application Ser. No. 15/196,643, filed on Jun. 29, 2016, which claims the benefit of U.S. Provisional Application No. 62/240,339, filed on Oct. 12, 2015. The disclosures of the above applications are incorporated herein by reference in their entirety.

BACKGROUND

Various systems require electrical coupling between electrical devices disposed within a hermetically sealed enclosure and external devices. Oftentimes, such electrical coupling needs to withstand various environmental factors such that a conductive pathway or pathways from an external surface to within the enclosure remains stable. For example, implantable medical devices (IMDs), e.g., cardiac pacemakers, defibrillators, neurostimulators and drug pumps, which can include electronic circuitry and battery elements, require an enclosure or housing to contain and hermetically seal these elements within a body of a patient. Many of these IMDs include one or more electrical feedthrough assemblies to provide electrical connection between the elements contained within the housing and components of the IMD external to the housing. For example, one or more sensors, electrodes, and lead wires can be mounted on an exterior surface of the housing and electrically connected to one or more elements disposed within the housing. Further, electrical contacts can be housed within a connector header that is mounted on the housing to provide coupling for one or more implantable leads, which typically carry one or more electrodes or other types of physiological sensors. A physiological sensor, for example a pressure sensor, incorporated within a body of a lead may also require a hermetically sealed housing to contain electronic circuitry of the sensor and an electrical feedthrough assembly to provide electrical connection between one or more lead wires, which extend within the implantable lead body, and the contained circuitry.

A feedthrough assembly typically includes one or more feedthrough pins that extend from an interior to an exterior of the housing through a ferrule. Each feedthrough pin is electrically isolated from the ferrule, and, for multipolar assemblies, from one another, by an insulator element, e.g., glass or ceramic, that is mounted within the ferrule and surrounds the feedthrough pin(s). Glass insulators are typically sealed directly to the pin(s) and to the ferrule, e.g., by heating the assembly to a temperature at which the glass wets the pin(s) and ferrule, while ceramic insulators are typically sealed to the pin(s) and to the ferrule by a braze joint. High temperatures are typically required to join corrosion-resistant conductive materials with corrosion-resistant insulative materials. Such high temperatures, however, can alter the physical properties of the conductive and insulative materials. Further, feedthroughs formed in the housing can allow external environmental elements to leak into the interior of the housing.

SUMMARY

In general, the present disclosure provides various embodiments of a sealed package and a method of forming such package. In one or more embodiments, the sealed package includes a housing extending along a housing axis between a first end and a second end, an electronic device disposed within the housing and including a device contact, and an external contact sealed to the housing at the first end of the housing. The package can also include a conductive member compressed between the external contact and the device contact such that the conductive member electrically couples the electronic device to the external contact.

In one aspect, the present disclosure provides a hermetically-sealed package that includes a housing extending along a housing axis between a first end and a second end, and an electronic device disposed within the housing that includes a device contact. The package also includes an external contact hermetically sealed to the housing at the first end of the housing, and a conductive member electrically connected to the external contact and the device contact such that the conductive member electrically connects the electronic device to the external contact. The conductive member is compressed between the external contact and the device contact.

In another aspect, the present disclosure provides a method of forming a hermetically-sealed package that includes a housing extending along a housing axis between a first end and a second end. The method includes disposing an electronic device within the housing, and electrically connecting a device contact of the electronic device to a conductive member. The method further includes compressing the conductive member between an external contact and the device contact such that the conductive member electrically connects the electronic device to the external contact, and hermetically sealing the external contact to the housing at the first end of the housing.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
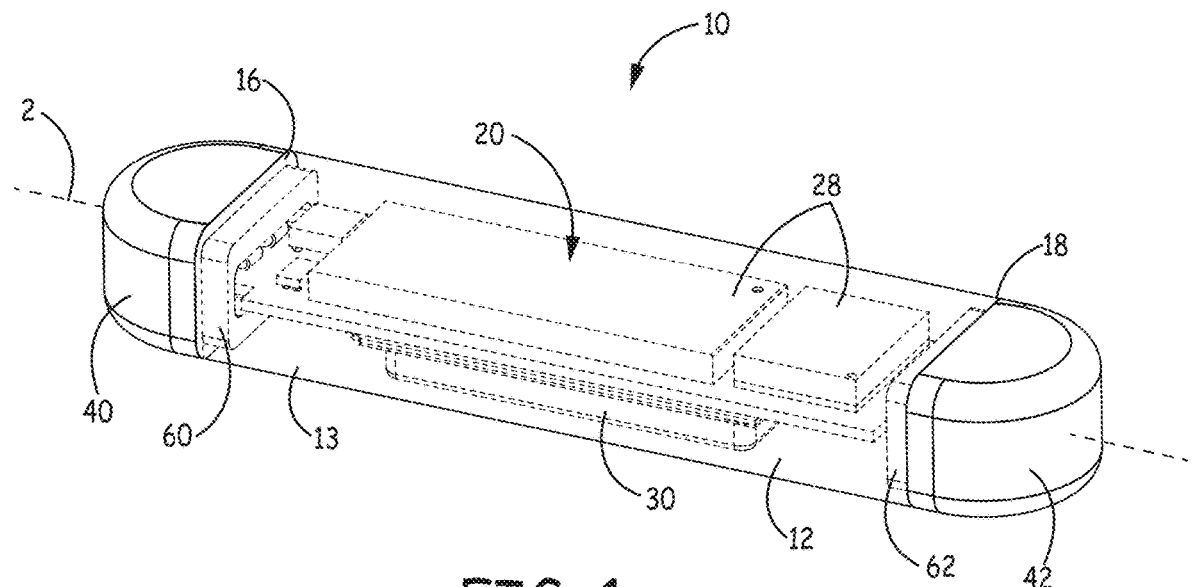
FIG. 1 is a schematic perspective view of one embodiment of a sealed package.
Figure 2:
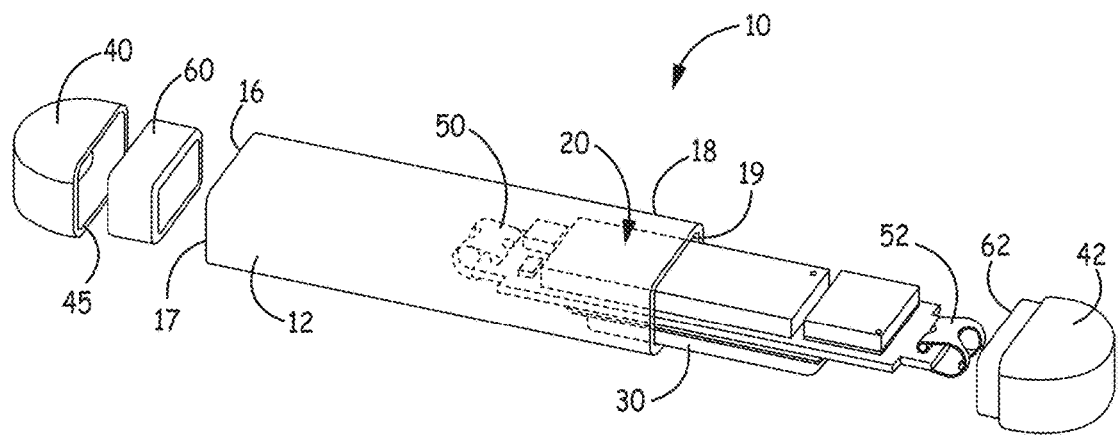
FIG. 2 is a schematic exploded view of the sealed package of FIG. 1.
Figure 3:
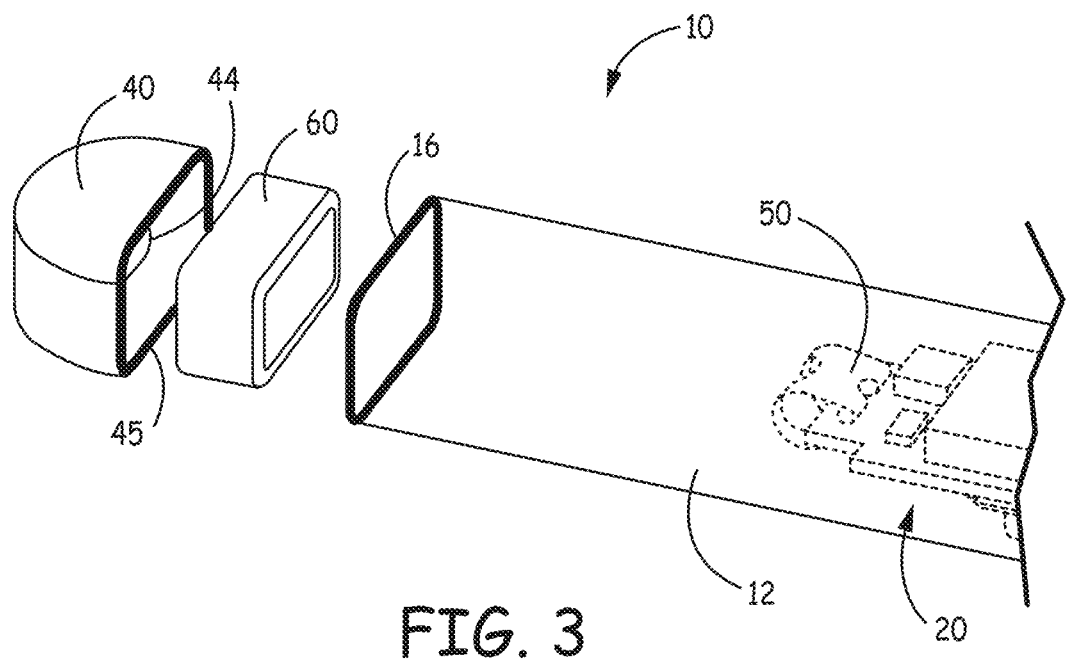
FIG. 3 is a schematic exploded view of a portion of the sealed package of FIG. 1.

In general, the present disclosure provides various embodiments of a sealed package and a method of forming such package. In one or more embodiments, the sealed package includes a housing extending along a housing axis between a first end and a second end, an electronic device disposed within the housing and including a device contact, and an external contact sealed to the housing at the first end of the housing. The package can also include a conductive member compressed between the external contact and the device contact such that the conductive member electrically couples the electronic device to the external contact.

The various embodiments of sealed packages described herein can include or be utilized with any device or system that requires sealed conductive pathways. For example, one or more embodiments of sealed packages described herein can include an implantable medical device or system disposed within the sealed package. Further, in one or more embodiments, the sealed package can be electrically connected to an implantable medical device or other system external to the package. Nearly any implantable medical device or system employing leads may be used in conjunction with the various embodiments of sealed packages described herein. Representative examples of implantable medical devices included in or utilized with the various embodiments of sealed packages described herein include hearing implants, e.g., cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like.

One or more embodiments of sealed packages described herein can provide an external contact that electrically connects electronic devices disposed within a sealed housing with, e.g., tissue of a patient, an external electronic device, a lead or other conductor, etc. The electronic device can include one or more power sources. Further, in one or more embodiments, the sealed package can provide this connection between internal devices disposed within the housing and external tissue or components without forming a feedthrough in the housing. In embodiments where the housing includes a material or materials that are transparent to a desired wavelength or range of wavelengths of electromagnetic radiation, one or more optical sensors can be disposed within the housing that are adapted to detect one or more environmental conditions through the housing without having to dispose such sensors to an external surface of the housing and electrically connect the sensors to devices disposed within the housing. Further, one or more embodiments of sealed packages described herein can more easily provide power transfer through the housing of the package utilizing, e.g., inductive, radio-frequency, or optical (e.g., photovoltaic) techniques.

Figure 4:
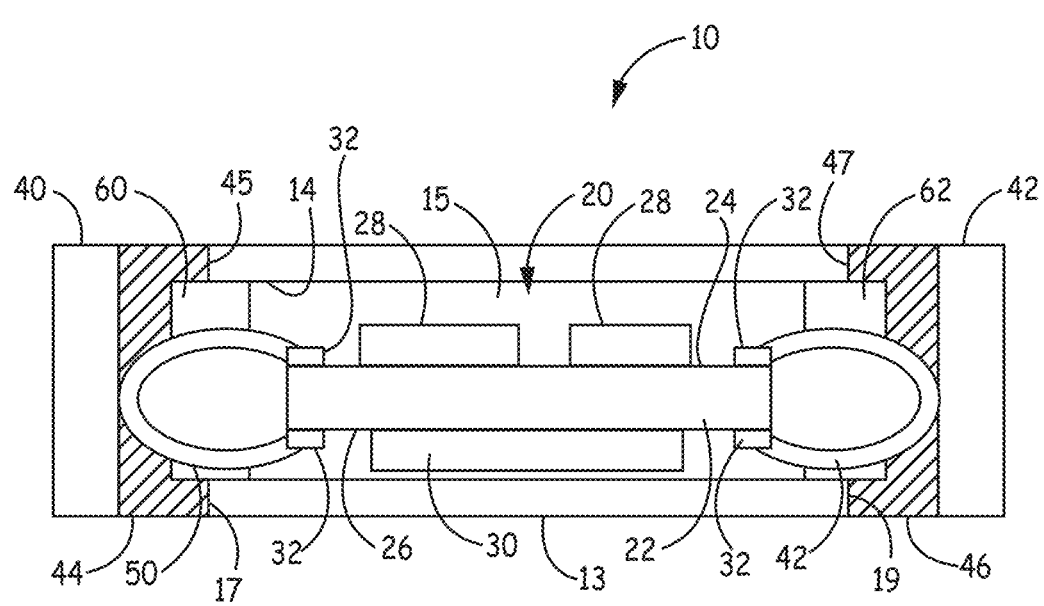
FIG. 4 is a schematic cross-section view of the sealed package of FIG. 1.

FIGS. 1-4 are various schematic views of one embodiment of a sealed package 10. The sealed package 10 can include a housing 12, one or more electronic devices 20 disposed within the housing, and an external contact 40 sealed to the housing at a first end 16 of the housing. In one or more embodiments, the sealed package 10 can also include a conductive member 50 electrically connected to the external contact 40 and a device contact 32 (FIG. 4). The conductive member 50 can electrically connect the electronic device 20 to the external contact 40. In one or more embodiments, the conductive member 50 can be compressed between the external contact 40 and the device contact 32 to provide this electrical connection between the electronic device 20 and the external contact.

The housing 12 can extend along a housing axis 2 between the first end 16 and a second end 18 of the housing. The housing 12 can take any suitable shape or combination of shapes. For example, the housing 12 can take any suitable shape in a plane orthogonal to the housing axis 2. In the embodiment illustrated in FIGS. 1-4, the housing 12 takes a rectangular shape in a plane orthogonal to the housing axis 2. Further, for example, the housing 12 can take any suitable shape or combination of shapes in a plane parallel to the housing axis 2. In the illustrated embodiment, the housing 12 takes a rectangular shape in a plane parallel to the housing axis 2. Further, the housing 12 can be a single, unitary housing. In one or more embodiments, the housing 12 can include two or more sections that are connected together using any suitable technique or combination of techniques.

In general, the housing 12 can have any suitable dimensions, e.g., the housing can have any suitable length as measured in a direction parallel to the housing axis 2. The housing 12 can be hollow to form a cavity 15 (FIG. 4). The cavity 15 can have any suitable dimensions such that one or more electronic devices 20 can be disposed within the housing. In such embodiments, the housing 12 can have any suitable thickness as measured between an outer surface 13 and an inner surface 14. In one or more embodiments, the housing 12 can be solid, and the one or more electronic devices 20 can be encased within the housing.

The housing 12 can include any suitable material or combination of materials, e.g., metal, polymeric, ceramic, or inorganic materials. In one or more embodiments, the housing 12 can include at least one of glass, quartz, silica, sapphire, silicon carbide, diamond, and gallium nitride. In one or more embodiments, the housing 12 can include at least one of copper, silver, titanium, niobium, zirconium, tantalum, stainless steel, platinum, iridium. Further, in one or more embodiments, the housing 12 can include biocompatible materials such that the package 10 can be implanted within a patient's body. Further, one or more coatings or layers can be disposed on the outer surface 13 of the housing 12 that provide biocompatibility. In one or more embodiments, the housing 12 can be electrically conductive to provide a ground electrode for the package 10 as is known in the art. In one or more embodiments, the housing 12 can be nonconductive.

Further, at least a portion of the housing 12 can be substantially transparent at a desired wavelength or range of wavelengths. As used herein, the phrase "substantially transparent" means that the substrate transmits greater than 50% of electromagnetic radiation incident on the substrate for a selected wavelength or range of wavelengths. In one or more embodiments, the housing 12 can be substantially transmissive to electromagnetic radiation having a wavelength in a range of 200 nm to 10000 nm. In one or more embodiments, the housing 12 can be substantially transmissive to at least one of UV light, visible light, and IR light. In one or more embodiments, at least a portion of the housing 12 can be substantially transparent such that the electronic device 20 can include one or more optical sensors that can be utilized to detect one or more preselected external conditions, e.g., blood oxygen levels.

Disposed within the housing 12 is the electronic device 20. Electronic device 20 can include any suitable component or components, electronic circuitry, and one or more conductors that electrically connect the components and circuitry to each other and to one or more conductive members 50, 52. In the embodiment illustrated in FIGS. 1-4, electronic device 20 includes components 28 disposed on a first major surface 24 of a substrate 22, and a power source 30 disposed on a second major surface 26 of the substrate (FIG.

4). The components 28 can each include any suitable component or electronic circuitry, e.g., capacitors, transistors, integrated circuits, including controllers and multiplexers, sensors, etc. Although depicted as being disposed on the first major surface 24, the components 28 can be disposed on the second major surface 26, or the components can be disposed on both the first and second major surfaces. Further, any suitable number of components can be disposed on one or both of the first and second major surfaces 24, 26. In one or more embodiments, the electronic device 20 can be electrically connected to other electronic circuitry or devices disposed on or adjacent the substrate 22 or within the housing 12.

Any suitable technique or combination of techniques can be utilized to dispose the components 28 on the substrate 22. In one or more embodiments, the components 28 can be formed on or in the substrate 22. In one or more embodiments, the components 28 can be formed separately and then attached to the substrate 22 using any suitable technique or combination of techniques, e.g., a bond can be formed between each component and the substrate.

Further, the electronic device 20 includes power source 30 disposed on the second major surface 26 of the substrate 22. The electronic device 20 can include any suitable number of power sources 30. The power source 30 can include any suitable power source or combination of power sources, e.g., one or more batteries, capacitors, inductive-coupled energy devices, photovoltaic devices, betavoltaic devices, alphavoltaic devices, and thermo-electric devices. The power source 30 can be disposed on one or both of the first and second major surfaces 24, 26 of the substrate 22. The power source 30 can be disposed on the same major surface as the components 28 or on a different major surface. In one or more embodiments, the power source 30 can be disposed within the housing 12 separate from substrate 22.

The power source 30 can be electrically connected to one or more of the components 28 using any suitable technique or combination of techniques, e.g., one or more vias can be formed between the first major surface 24 and second major surface 26 of substrate 22, and conductive material can be disposed within one or more of the vias to provide an electrical pathway to connect the power source 30 to one or more of the components 28.

As mentioned herein, the electronic device 20 can include one or more sensors, e.g., one or more optical sensors. In one or more embodiments, at least a portion of the housing 12 can be transparent such that an optical sensor disposed on the substrate 22 or within the cavity 15 of the housing can detect one or more external conditions, e.g., from a patient when the package 10 is disposed within the patient. For example, the electronic device 20 can include an infrared or near-infrared oxygen sensor that can detect through the housing 12 the oxygen level of the blood of the patient.

The electronic device 20 can also include one or more device contacts 32 disposed on or in one or both of the first major surface 24 and second major surface 26 of the substrate 22. The device contacts 32 can be electrically connected to one or more components 28 and the power source 30 using any suitable technique or combination of techniques, e.g., one or more conductors can be disposed on one or both of the first and second major surfaces 24, 26 of the substrate 22 that electrically connect one or more of the device contacts 32 to one or more of the components 28 and power source 30. Each component 28 can include one or more component contacts (not shown) that are electrically connected to one or more of the device contacts 32. Similarly, in one or more embodiments, the power source 30 can include one or more power source contacts (not shown) that are electrically connected to one or more of the device contacts 32. Further, for example, solder bumps and/or contact pads of one or more components 28 and power source 30 can be directly attached to one or more contacts 32 using any suitable technique or combination of techniques, e.g., soldering, welding, laser bonding, wire bonding, etc.

The contacts 32 can take any suitable shape or combination of shapes and be disposed in any suitable location on or in the substrate 22 of the electronic device 20. Any suitable technique or combination of techniques can be utilized to form device contacts 32, e.g., chemical vapor deposition, plasma vapor deposition, physical vapor deposition, etc., followed by photolithography, chemical etching, electroplating, immersion plating, etc. Further, the device contacts 32 can include any suitable conductive material or combination of conductive materials.

The substrate 22 can include any suitable material or combination of materials. In one or more embodiments, the substrate 22 can be a non-conductive or insulative substrate such that the components 28, device contacts 32, power source 30, and any conductors or other devices disposed on the substrate can be electrically isolated if desired. In one or more embodiments, the substrate 22 can include at least one of glass, quartz, silica, sapphire, silicon carbide, diamond, gallium nitride, and organic materials, or any combinations thereof. In one or more embodiments, the substrate 22 can include the same material or materials as the housing 12.

The package 10 can also include an external contact 40 and a second external contact 42. Although depicted as included two external contacts 40, 42, the package 10 can include any suitable number of external contacts, e.g., one, two, three, four, five, six, or more external contacts. The external contacts 40, 42 can take any suitable shape or combination of shapes and have any suitable dimensions. In general, the external contacts 40, 42 can provide greater conductive surface area than external electrodes that may be included in traditional feedthrough assemblies. Further the external contacts 40, 42 can include any suitable material or combination of conductive materials, e.g., copper, silver, titanium, niobium, zirconium, tantalum, stainless steel, platinum, iridium, or combinations thereof. In one or more embodiments, the external contacts 40, 42 can include two or more materials, e.g., bi-metals, clad laminates, etc. The external contact 40 can include the same material as the second external contact 42 or material that is different from a material of the second external contact.

The external contact 40 can be sealed to the housing 12 at the first end 16 of the housing. Further, the second external contact 42 can be sealed to the housing 12 at the second end 18 of the housing. In one or more embodiments, one or both of the external contact 40 and the second external contact 42 can be hermetically sealed to the housing 12. For example, in one or more embodiments, one or both of the external contacts 40, 42 can be hermetically sealed to the housing 12 by a bond. Any suitable technique or combination of techniques can be utilized to form such bond, e.g., the techniques described in co-owned U.S. patent application Ser. No. 14/976,475 (Medtronic Reference No. C00008775.USU2), entitled RAPID ROOM-TEMPERATURE PATTERNED TRANSPARENT MATERIAL-ABSORBENT OPAQUE MATERIAL SURFACE BONDING. For example, electromagnetic radiation (e.g., light) can be directed through the housing 12 from the outer surface 13 and focused at a region between a mating surface 17 of the housing and a mating surface 45 of the external contact 40. Further, electromagnetic radiation can be directed through the housing 12 from the outer surface 13 and focused at a region between a second mating surface 19 of the housing and a mating surface 47 of the second external contact 42. Any suitable electromagnetic radiation can be utilized to form the bond. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 10,000 nm. For example, laser light can include UV light, visible light, IR light, and combinations thereof. In one or more embodiments, a UV laser can be utilized to provide light having a wavelength of about 300 nm and a pulse width of 10 ns. In one or more embodiments, the materials for the external contacts 40, 42 and the housing 20, and the power level and wavelength of the light used may be selected such that the light may not directly damage, ablate, warp, or cut the external contacts and the housing, and such that the external contacts and the housing retain their bulk properties.

In general, light can be provided by any suitable laser or laser system. For example, the laser may generate light having a relatively narrow set of wavelengths (e.g., a single wavelength). The light emitted by the laser may form a collimated beam that may not be focused at a particular point. The light emitted by the laser may be focused at a focal point at a region between the first major surface 13 of the housing 12 and one or both external contacts 40, 42 to generate a laser bond. One or both of the external contacts 40, 42 can also include a recessed portion (not shown) that is adapted to be inserted into the housing 12 at the respective end, and the laser bond can be formed between the housing and the recessed portion of each external contact.

Although the laser may provide light that has a narrow range of wavelengths, in one or more embodiments, the laser may represent one or more devices that emit light having a wider range of wavelengths than a single typical laser. A wide variety of devices may be used to emit light having a narrow or wide range of wavelengths. In one or more embodiments, the laser may include one or more laser devices including diode and fiber lasers. Laser sources may also include, e.g., TI sapphire, argon ion, Nd:YAG, XeF, HeNe, Dye, GaAs/AlGaAs, $CO_2$, Alexandrite, InGaAs, InGaAsP, Nd:glass, Yb:YAG, or Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 μm, with a top hat or Gaussian spatial energy profile.

In one or more embodiments, the bond can include an interfacial layer between one or both of the external contacts 40, 42 and the housing 12. This interfacial layer can have any suitable thickness in a direction parallel to the housing axis 2. In one or more embodiments, the interfacial layer has a thickness in a direction parallel to the housing axis 2 of no greater than 50 nm, 100 nm, 150 nm, or 200 nm.

One or both of the external contacts 40, 42 can be utilized to electrically connect the electronic device 20 to any suitable device or system that are external to the package 10. For example, one or both of the external contacts 40, 42 can electrically connect the electronic device 20 to a lead of an implantable medical device as is further described herein. In one or more embodiments, one or both of the external contacts 40, 42 can electrically connect the electronic device 20 to one or more additional power sources. Further, in one or more embodiments, one or both of the external contacts 40, 42 can be therapeutic electrodes that can be utilized for delivering and/or receiving one or more electric signals to or from a patient, either while the package is external or internal to a patient. Any suitable technique or combination of techniques can be utilized to electrically connect the electronic device 20 to one or more devices through one or both of the external contacts 40, 42, e.g., soldering, physical contact, welding, etc.

The package 10 can also include an alignment insert 60 that extends from the first end 16 of the housing 12 such that the alignment insert is disposed within the housing and the external contact 40. Further, in one or more embodiments, the package 10 can also include a second alignment insert 62 that extends from the second end 18 of the housing 12 such that the second alignment insert is disposed within the housing and the second external contact 42. The alignment inserts 60, 62 can assist in aligning the external contacts 40, 42 with the housing 12 such that the external contacts can be sealed to the housing at the first and second ends 16, 18 respectively. Further, the alignment inserts 60, 62 can provide a friction-fit with the external contacts 40, 42, and the housing 12. The alignment inserts 60, 62 can take any suitable shape or combination of shapes and dimensions, e.g., the same shape and dimension as the inner surface 14 of the housing 12. Further, the alignment inserts 60, 62 can include any suitable material or combination of materials. In one or more embodiments, the alignment insert 60 can be attached to at least one of the external contact 40 and the housing 10 using any suitable technique or combination of techniques. Further, the second alignment insert 62 can be attached to at least one of the second external contact 42 and the housing 10 using any suitable technique or combination of techniques.

One or both of the external contacts 40, 42 can be electrically connected to the electronic device 20 using any suitable technique or combination of techniques. In one or more embodiments, the package 10 can include a conductive member 50 that is electrically connected to the external contact 40 and one or more device contacts 32 such that the conductive member electrically connects the electronic device 20 to the external contact. Further, in one or more embodiments, the package 10 can also include a second conductive member 52 that is electrically connected to the second external contact 42 and one or more device contacts 32 such that the second conductive member electrically connects the electronic device 20 to the second external contact. Although depicted as including two conductive members 50, 52, the package can include any suitable number of conductive members that electrically connect the electronic device 20 to an external contact, e.g., one, two, three, four, five, six, or more conductive members.

The conductive members 50, 52 can take any suitable shape or combination of shapes and include any suitable dimensions. Further, the conductive members 50, 52 can include any suitable material or combination of conductive materials, e.g., copper, silver, titanium, niobium, zirconium, tantalum, stainless steel, platinum, iridium, BeCu, gold, nickel, brass, or combinations thereof. In one or more embodiments, one or both of the conductive members 50, 52 can include an insulative or dielectric substrate that is plated with a conductive material or materials. The conductive member 50 can include the same material as the second conductive member 52 or material different from a material of the second conductive member. In one or more embodiments, one or both of the conductive member 50 and second conductive member 52 can include a resilient material that can be compressed and provide a biasing force. In one or more embodiments, the biasing force can be in a direction along the housing axis 2 away from the electronic device 20 and toward the respective external contact 40, 42 that is associated with the conductive member 50, 52.

In embodiments where the conductive members 50, 52 include a resilient material, the external contacts 40, 42 can be electrically connected to the electronic device 20 by pressing the contacts against the respective conductive member and sealing the contacts to the housing 12. The conductive members 50, 52 can be compressed between the external contacts 40, 42 and one or more device contacts 32. For example, the conductive member 50 can be compressed between an inner surface 44 of the external contact 40 and one or more device contacts 32 such that the conductive member electrically connects the external contact to the electronic device 20. Further, for example, the second conductive member 52 can be compressed between an inner surface 46 of the external contact 42 and one or more device contacts 32 such that the second conductive member electrically connects the external contact to the electronic device 20. In one or more embodiments, a non-bonded electrical connection can be formed between the external contact 40 and the electronic device 20 utilizing the conductive member 50. As used herein, the term "non-bonded electrical connection" means that an electrical connection is formed between one or more contacts, terminals, electrodes, etc., that can be maintained without the use of a chemical bonding technique, e.g., adhering, soldering, welding, etc. Further, in one or more embodiments, a non-bonded electrical connection can be formed between the second external contact 42 and the electronic device 20 utilizing the second conductive member 52.

The conductive members 50, 52 can be electrically connected to the electronic device 20 using any suitable technique or combination of techniques. For example, in one or more embodiments, conductive member 50 can be electrically connected to the electronic device 20 through one or more device contacts 32. Further, in one or more embodiments, the conductive member 52 can be electrically connected to the electronic device 20 through one or more device contacts 32. The conductive members 50, 52 can be electrically connected to one or more device contacts 32 using any suitable technique or combination of techniques, e.g., soldering, mechanical fastening, bonding with an electrical adhesive, etc.

Figure 5:
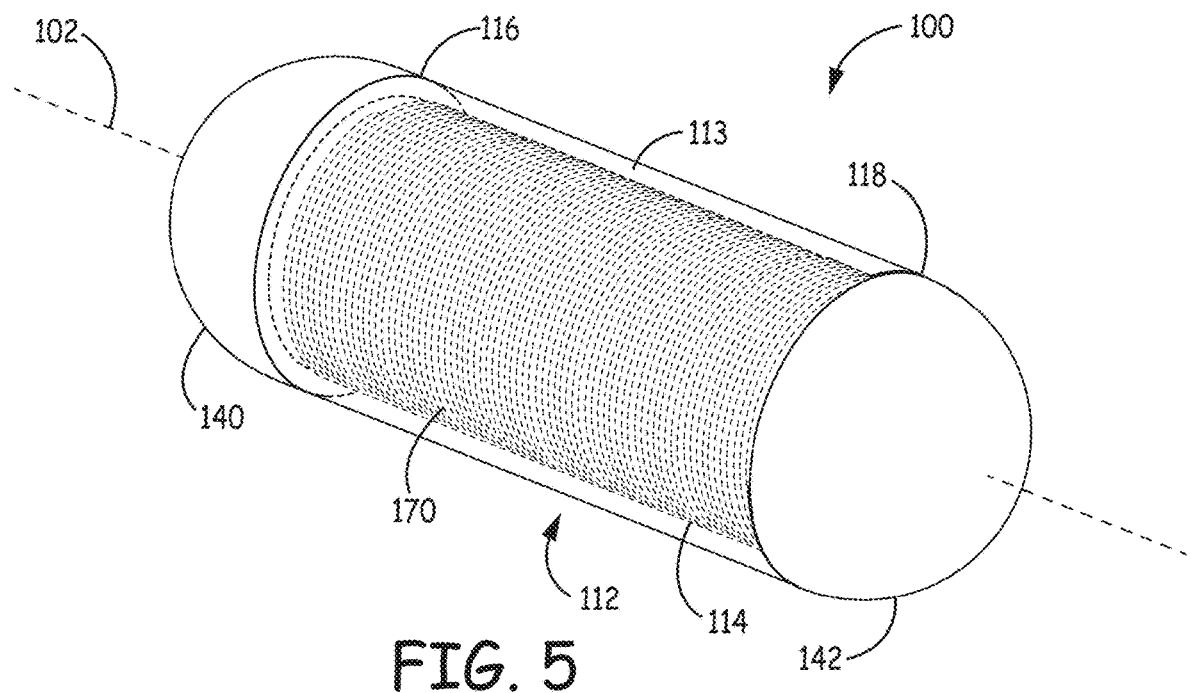
FIG. 5 is a schematic perspective view of another embodiment of a sealed package.

Although not shown, the package 10 can include any suitable additional electronic devices, electronic circuitry, and conductors disposed on one or both of the outer surface 13 and the inner surface 14 of the housing 12. For example, FIG. 5 is a schematic perspective view of another embodiment of a sealed package 100. All of the design considerations and possibilities regarding the sealed package 10 of FIGS. 1-4 apply equally to the package 100 of FIG. 5. The package 100 includes a housing 112 and electronic device (not shown) disposed within the housing. The electronic device can include one or more device contacts (e.g., device contacts 32 of FIGS. 1-4) that are electrically connected to the electronic device. The package 100 also includes an external contact 140 and a second external contact 142. The external contacts 140, 142 can be sealed (e.g., hermetically sealed) to the housing 112 at first and second ends 116, 118 of the housing respectively. Although not shown, the package 100 can also include one or more conductive members disposed within the housing 112 that electrically connect one or both of the external contacts 140, 142 to one more device contacts of the electronic device such that the conductive members electrically connect the electronic device to one or both of the external contacts. In one or more embodiments, these conductive members can be compressed between the external contacts 140, 142 and one or more device contacts.

One difference between package 100 and package 10 of FIGS. 1-4 is that a conductor 170 is disposed on an inner surface 114 of the housing 112. The conductor 170 can take any suitable shape or combination of shapes and have any suitable dimensions. Further, the conductor 170 can include any suitable conductive material or combination of materials, e.g., the same materials described herein regarding external contacts 40, 42 of package 10 of FIGS. 1-4. Although shown as disposed on the inner surface 114 of housing 112, conductor 170 can be disposed on an outer surface 113 of the housing, or on both the inner surface and the outer surface of the housing. Further, the conductor 170 can include any suitable number of conductors, e.g., 1, 2, 3, 4, or more discrete conductors.

In one or more embodiments, the conductor 170 can be formed to provide an antenna, and the package 100 can be wirelessly coupled to a device or system through such antenna. Further, in one or more embodiments, the conductor 170 can form an inductive coil that can be utilized to provide inductive coupling to one or more external devices, e.g., one or more inductive power sources. In one or more embodiments, the conductor 170 can include an electromagnetic interference shield that aids in shielding the electronic device disposed within the housing 112 from undesirable electromagnetic radiation that is incident upon the package 100.

The conductor 170 can be electrically connected to one or more components or power sources of the electronic device disposed within the housing 112 of the package 100 using any suitable technique or combination of techniques. For example, if one or more conductors 170 are disposed on the outer surface 113 of the housing 112, a via or vias can be formed between the outer surface and the inner surface 114 of the housing. Conductive material can be disposed within such via or vias that electrically connects the conductor 170 to the electronic device. The conductor 170 can be electrically connected to the vias using any suitable technique or combination of techniques. In embodiments where the conductor 170 is disposed on the inner surface 114 of the housing or on 112, the conductor can be electrically connected to the electronic device using any suitable technique or combination of techniques, e.g., a lead wire or wires can be connected to the conductor and the electronic device.

Another difference between package 100 of FIG. 5 and package 10 of FIGS. 1-4 is that the housing 112 takes an elliptical shape in a plane orthogonal to a housing axis 102. Further, external contacts 140, 142 each take an elliptical cross-sectional shape in a plane orthogonal to the housing axis 102 and in a plane substantially parallel to the housing axis.

Figure 6:
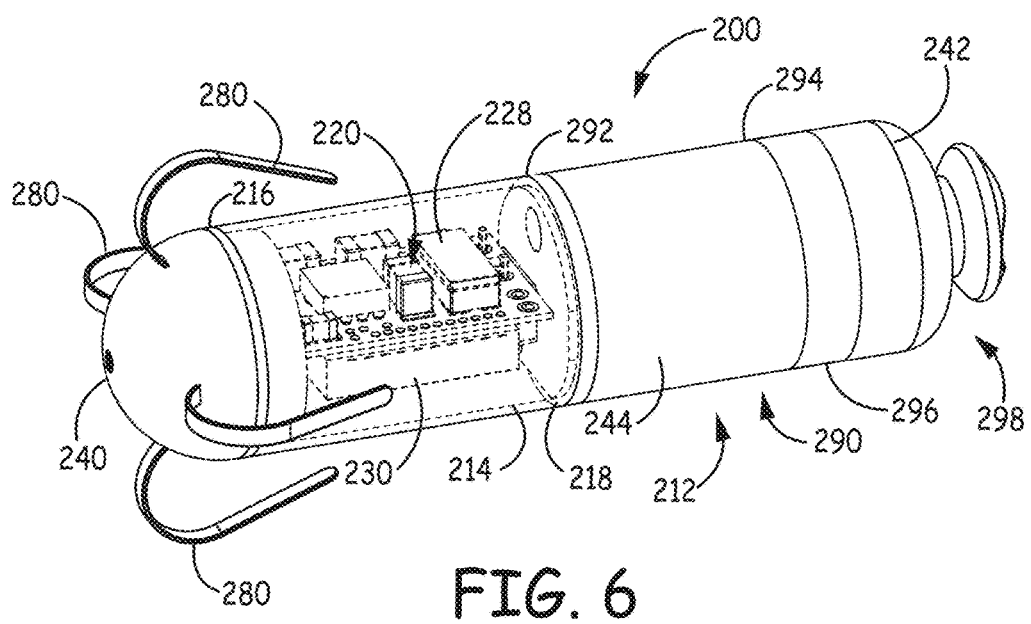
FIG. 6 is a schematic perspective view of another embodiment of a sealed package.

As mentioned herein, the various packages of the present disclosure can be implanted within a patient to provide any suitable therapeutic treatment to the patient. Any suitable technique or combination of techniques can be utilized to implant the package within the body such that the package remains in the desired location. For example, FIG. 6 is a schematic perspective view of another embodiment of a package 200. All of the design considerations and possibilities regarding the package 10 of FIGS. 1-4 and the package 100 of FIG. 5 apply equally to the package 200 of FIG. 6. One difference between package 200 of FIG. 6 and package 10 of FIGS. 1-4 is that housing 212 includes a transparent portion 214 that is connected to an opaque portion 290. In one or more embodiments, a second end 218 of the transparent portion 214 is connected to a first end 292 of the opaque portion 290. Any suitable technique or combination of techniques can be utilized to connect the transparent portion 214 to the opaque portion 290, e.g., the same techniques described herein for sealing the external contacts 40, 42 to the housing 12 of sealed package 10 of FIGS. 1-4.

The transparent portion 214 of the housing 212 can include any suitable material or combination of materials that are transparent to one or more wavelengths of electromagnetic radiation, e.g., the same transparent materials described herein regarding housing 12 of package 10. The transparent portion 214 can take any suitable shape or combination of shapes, e.g., the same shapes described herein regarding housing 12 of package 10. Further, the opaque portion 290 of housing 212 can take any suitable shape or combination of shapes, e.g., the same shapes described herein regarding housing 12 of package 10. Further, the opaque portion 290 can include any suitable material or combination of materials, e.g., metal, polymer, etc.

In one or more embodiments, the package 200 can include an external contact 240, a second external contact 242, and a third external contact 244. The external contacts 240, 242, 244 can be disposed in any suitable location on or adjacent the transparent portion 214, the opaque portion 290, or both the transparent portion and opaque portion of the housing 212. As illustrated in FIG. 6, the external contact 240 is disposed at a first end 216 of the transparent portion 214 of the housing 212 such that it is connected to the transparent portion 214. Further, the second external contact 242 is disposed at a second end 298 of the housing 212. And the third external contact 244 is disposed on or in the opaque portion 290 of the housing 212. In one or more embodiments, the opaque portion 290 of the housing 212 can provide the third external contact 244, e.g., the opaque portion can include conductive material to provide the third external contact. In one or more embodiments, the second external contact 242 can be electrically isolated from the third external contact 244 by an electrically insulative material 296 disposed between the second external contact and the third external contact. The electrically insulative material 296 can include any suitable material or combination of materials that can isolate the second external contact 242 from the third external contact 244.

The package 200 can include an electronic device 220 disposed within the housing 212 in any suitable location. As illustrated in FIG. 6, the electronic device 220 is disposed at least partially within the transparent portion 214 of the housing 212. In one or more embodiments, additional electronic devices can be disposed within the opaque portion 290 of the housing 212. Further, in one or more embodiments, the electronic device 220 can include a power source 220 that is electrically connected to one or more components of the electronic device 220. Further, in one or more embodiments, the power source 230 can be electrically connected to one or more of the external contacts 240, 242, 244. In one or more embodiments, the opaque portion 290 of the housing 212 can be a power source that is formed and then connected to the transparent portion 214.

The electronic device 220 can be electrically connected to one or more the external contacts 240, 242, 244 using any suitable technique or combination of techniques. For example, in one or more embodiments, a conductive member (e.g., conductive member 50 of FIGS. 1-4) can be disposed between the electronic device 220 and the external contact 240 such that the conductive member electrically connects the electronic device to the external contact. In one or more embodiments, the conductive member can provide a non-bonded electrical connection between the external contact 240 and the electronic device 220 by compressing the external contact against the conductive member as is described herein regarding conductive member 50 of FIGS. 1-4.

In one or more embodiments, the package 200 can include a second conductive member (e.g., second conductive member 52 of FIGS. 1-4) can be disposed between the electronic device 220 and one or both of the second and third external contacts 242, 244 such that the conductive member electrically connects the electronic device to the external contacts. In one or more embodiments, the conductive member can provide a non-bonded electrical connection between one or both of the second and third external contacts 242, 244 and the electronic device 220 by compressing the external contact against the conductive member as is described herein regarding conductive member 52 of FIGS. 1-4. In one or more embodiments, one or more conductors can be disposed between the electronic device 220 and the second and third external contacts 242, 244 through or on the opaque portion 290 of the housing 212 to electrically connect the electronic device with the external contacts.

The package 200 can also include one or more tines 280 that are disposed in any suitable location on the housing 212. The tines 280 can be utilized to anchor the package 200 to tissue within a patient such that the package remains in the desired location after implantation. The tines 280 can take any suitable shape or combination of shapes. Further, the package 200 can include any suitable number of tines 280. The tines 280 can include any suitable material or combination of materials, e.g., the same materials described herein regarding the external contacts. In one or more embodiments, the tines 280 can be electrically connected to an external contact, e.g., external contact 240, to provide an electrical signal to tissue of a patient. In such embodiments, the tines 280 can be electrically connected to an external contact using any suitable technique or combination of techniques. In one or more embodiments, the tines 280 are integral with an external contact, e.g., external contact 240, i.e., the tines are not made separately and then attached to the external contact but instead are manufactured from the same starting material as the external contact. In one or more embodiments, the tines 280 can be attached to the external contact 240 using any suitable technique or combination of techniques. In one or more embodiments, the tines 280 can be electrically insulative.

Figure 7:
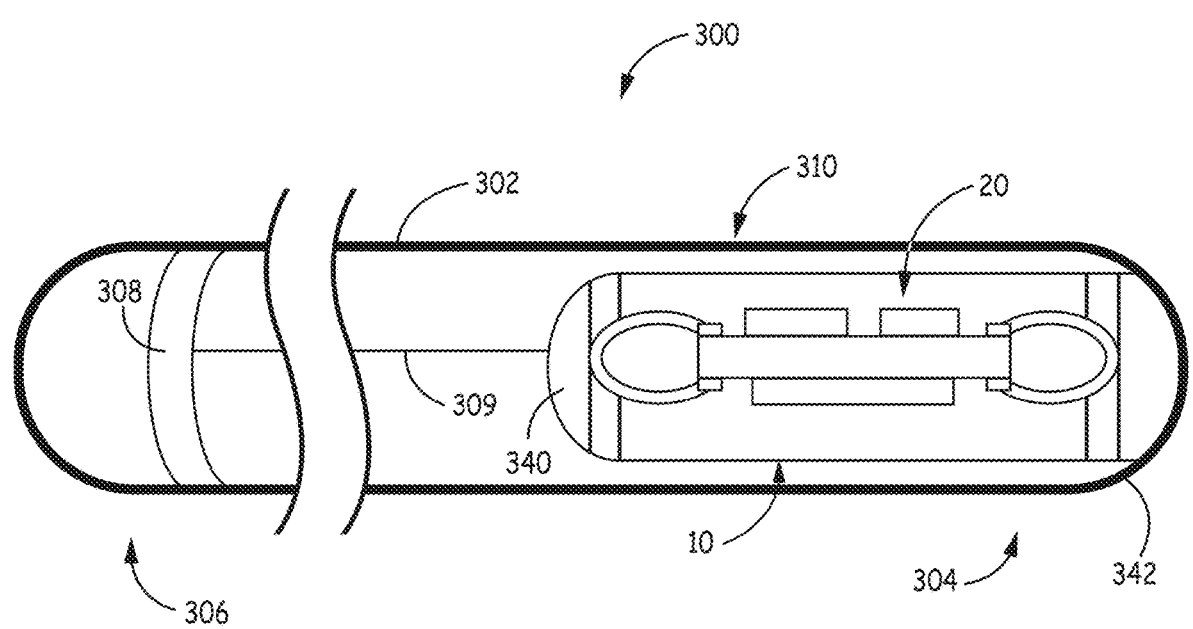
FIG. 7 is a schematic cross-section view of an implantable lead that includes the sealed package of FIG. 1.

The various embodiments of sealed packages described herein can be utilized with any system or device. For example, FIG. 7 is a schematic plan view of one embodiment of a lead 300. The lead 300 can be any suitable lead known in the art. Further, the lead 300 can be utilized with any suitable external medical device or implantable medical device. The lead 300 includes a lead body 302 that has a distal portion 304 and a proximal portion 306 that includes one or more discrete contacts 308.

Lead 300 also includes a sealed package, e.g., the sealed package 10 of FIGS. 1-4, disposed on or in the distal portion 304 of the lead body 302. Although the lead 300 is illustrated as including the sealed package 10 of FIGS. 1-4, any sealed package can be utilized with the lead.

In one or more embodiments, the discrete contact 308 of the lead 300 can be electrically coupled to the package 10 using any suitable technique or combination of techniques. In one or more embodiments, the discrete contact 308 of the lead 300 can be electrically coupled to the package 10 through one or more conductors or filers 309 that are disposed on or within the lead body 302. The discrete contact 308 can be electrically coupled to the electronic device 20 of the package 10 through the filer 309 and external contact 40. The discrete contact 308 can be adapted to electrically contact the lead 300 to an external or implantable medical device.

In one or more embodiments, second external contact 42 can be a therapeutic electrode and provide one or more electrical signals to tissue of a patient. In one or more embodiments, one or more therapeutic electrodes can be electrically connected to the second external contact 42 to provide one or more electrical signals to tissue of a patient. Further, in one or more embodiments, one or more additional leads can be electrically connected to the second external contact 42 to provide one or more electrical signals to tissue of a patient.

Figure 8:
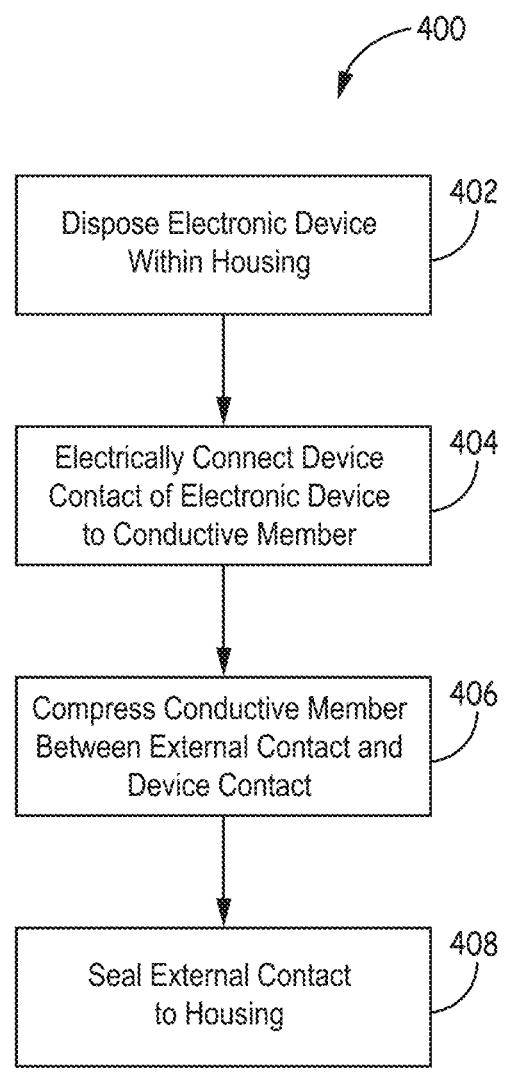
FIG. 8 is a flowchart of one embodiment of a method of forming a sealed package.

The various embodiments of sealed packages described herein can be formed using any suitable technique or combination of techniques. For example, FIG. 8 is a flowchart of one embodiment of a method 400 of forming a sealed package (e.g., package 10 of FIGS. 1-4). Although the method 400 will be described in reference to package 10, the method can be utilized to form any suitable sealed package.

At 402, the electronic device 20 can be disposed within the housing 12. The electronic device 20 can be formed using any suitable technique or combination of techniques and then disposed within the housing 12. At 404, one or more of the device contacts 32 can be electrically connected to at least one of conductive members 50, 52 using any suitable technique or combination of techniques. In one or more embodiments, the conductive members 50, 52 can be electrically connected to one or more of the device contacts 32 prior to disposing of the electronic device 20 within the housing 12. In one or more embodiments, the conductive members 50, 52 can be electrically connected to one or more of the device contacts 32 after the electronic device 20 has been disposed within the housing 12.

The conductive member 50 can be compressed between the external contact 40 and one or more device contacts 32 at 406 such that the conductive member electrically connects the electronic device 20 to the external contact. In one or more embodiments, the alignment sleeve 60 can first be inserted into the first end 16 of the housing 12 prior to compressing the conductive member 50 between the external contact 40 and the device contacts 32. Any suitable technique or combination of techniques can be utilized to compress the conductive member 50 between the external contact 40 and the device contacts 32.

In one or more embodiments, the second conductive member 52 can be compressed between the second external contact 42 and one or more device contacts 32 using any suitable technique or combination of techniques. Further, in one or more embodiments, the second alignment sleeve 62 can first be inserted into the second end 18 of the housing 12 prior to compressing the conductive member 52 between the second external contact 42 and device contacts 32. The second conductive member 52 can be compressed such that the conductive member electrically connects the electronic device 20 to the second external contact 42. In one or more embodiments, the electronic device 20 can be electrically connected to the second external contact 42 using any suitable technique or combination of techniques that do not require compression of a conductive member between the device contacts 32 and the external contact 62.

At 408, the external contact 40 can be sealed to the housing 12 at the first end 16 of the housing using any suitable technique or combination of techniques, e.g., laser bonding. In one or more embodiments, the external contact 40 can be hermetically sealed to the housing 12 at the first end 16 of the housing. Prior to sealing the external contact 40 to the housing 12, the mating surface 45 of the external contact and the mating surface 17 of the housing at the first end 16 can be polished using any suitable technique or combination of techniques. In one or more embodiments, the second external contact 42 can be sealed to the housing 12 at the second end 18 of the housing. In one or more embodiments, the second external contact 42 can be hermetically sealed to the housing 12 at the second end 18 of the housing. In one or more embodiments, the second external contact 42 can be sealed to the housing 12 at the second end 18 of the housing using any suitable technique or combination of techniques. Prior to sealing the second external contact 42 to the housing 12, the mating surface 46 of the second external contact and the mating surface 47 of the housing at the second end 18 can be polished using any suitable technique or combination of techniques.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A hermetically-sealed package comprising:
a housing extending along a housing axis between a first end and a second end and comprising an opaque portion and a transparent portion connected to the opaque portion;
an electronic device disposed within the housing;
an external contact hermetically sealed to the transparent portion of the housing at the first end of the housing and electrically connected to the electronic device; and
a tine adapted to anchor the hermetically-sealed package to tissue within a patient, wherein the tine is electrically connected to the external contact.

2. The package of claim 1, wherein the tine is integral with the external contact.

3. The package of claim 1, wherein the tine is attached to the external contact.

4. The package of claim 1, wherein the tine is adapted to provide an electrical signal to the tissue within the patient.

5. The package of claim 1, further comprising a conductive member electrically connected to the external contact and a device contact of the electronic device such that the conductive member electrically connects the electronic device to the external contact, wherein the conductive member is compressed between the external contact and the device contact.

6. The package of claim 1, further comprising a second external contact hermetically sealed to the opaque portion of the housing at the second end of the housing.

7. The package of claim 1, wherein the transparent portion of the housing is substantially transmissive to electromagnetic radiation having a wavelength in a range of 200 nm to 10000 nm.

8. The package of claim 1, wherein the transparent portion of the housing comprises sapphire.

9. The package of claim 1, wherein the external contact is hermetically sealed to the transparent portion of the housing by a laser bond.

10. The package of claim 1, wherein the transparent portion of the housing is hermetically sealed to the opaque portion of the housing by a laser bond.

11. The package of claim 1, further comprising a third external contact disposed on or in the opaque portion of the housing.

12. The package of claim 11, wherein the second external contact is electrically isolated from the third external contact by an electrically insulative material.

13. The package of claim 1, wherein the electronic device is disposed at least partially within the transparent portion of the housing.

14. The package of claim 1, wherein the electronic device comprises at least one of a power source, a multiplexer, a sensor, or a controller.

15. The package of claim 1, wherein the opaque portion of the housing comprises at least one of titanium, copper, silver, niobium, zirconium, tantalum, stainless steal, platinum, or iridium.

16. An implantable medical device system comprising:
a lead, wherein the lead comprises a lead body; and
the hermetically-sealed package of claim 1 disposed in a distal portion of the lead body.

17. The system of claim 16, wherein the external contact of the hermetically-sealed package is electrically coupled to a conductor of the lead.

18. A method of forming a hermetically-sealed package comprising a housing that extends along a housing axis between a first end and a second end and that comprises an opaque portion and a transparent portion, the method comprising:
disposing an electronic device within the housing;
electrically connecting a device contact of the electronic device to an external contact and a tine that is electrically connected to the external contact;
hermetically sealing the external contact to the transparent portion of the housing at the first end of the housing; and
hermetically sealing the transparent portion of the housing to the opaque portion of the housing.

19. The method of claim 18, wherein hermetically sealing the external contact to the transparent portion of the housing comprises forming a laser bond between the external contact and the transparent portion of the housing.

20. The method of claim 18, wherein hermetically sealing the transparent portion of the housing to the opaque portion of the housing comprises forming a laser bond between the transparent portion and the opaque portion.

* * * * *